United States Patent [19]

Ubukata et al.

[11] Patent Number: 5,437,978
[45] Date of Patent: Aug. 1, 1995

[54] DETECTION FOR STAPHYLOCOCCUS SPP.

[75] Inventors: Kimiko Ubukata, Tokyo; Satoru Nakagami, Hiroshima; Akio Yamane, Miyoshi, all of Japan

[73] Assignee: Wakunaga Seiyaku Kabushiki Kaisha, Osaka, Japan

[21] Appl. No.: 924,458

[22] Filed: Aug. 4, 1992

[30] Foreign Application Priority Data

Aug. 5, 1991 [JP] Japan .................... 3-195398

[51] Int. Cl.[6] ............ C12Q 1/68; C07H 19/10; C07H 21/00
[52] U.S. Cl. ..................... 435/6; 536/22.1; 536/23.1; 536/23.7; 536/24.3
[58] Field of Search ............ 435/6; 536/22.1, 23.1, 536/23.7, 24.3

[56] References Cited

U.S. PATENT DOCUMENTS 4,965,188 10/1990 Mullis et al. .................. 435/6

OTHER PUBLICATIONS

Song et al., "Evolution of an inducible . . . ", FEBS Lett., 221:1, pp. 167–171, 1987.

Blomster–Hautamaa et al., "The nucleotide and partial . . . ", JBC, 261:33, pp. 15783–15786, 1986.

*Primary Examiner*—Charles L. Patterson, Jr.
*Assistant Examiner*—Hyosuk Kim
*Attorney, Agent, or Firm*—Bacon & Thomas

[57] ABSTRACT

The present invention discloses a primer for detecting methicillin-resistant or toxic shock syndrome toxin-1 Staphylococcus spp. comprising any one of nucleotide fragments of sequences (1) to (4):

| | |
|---|---|
| 5'GAAATGACTGAACGTCCGAT | (1) |
| 5'GCGATCAATGTTACCGTAGT | (2) |
| 5'AGTATGGGCCAAAGTTCGAT | (3) |
| 5'CACTTTGATATGTGGATCCG | (4) | a method and kit for detecting these bacteria using the primer. The present invention makes direct and rapid detection of MRS and/or TPS from samples possible, and enables patients with infections caused by these bacteria to be treated at an early stage.

20 Claims, 2 Drawing Sheets

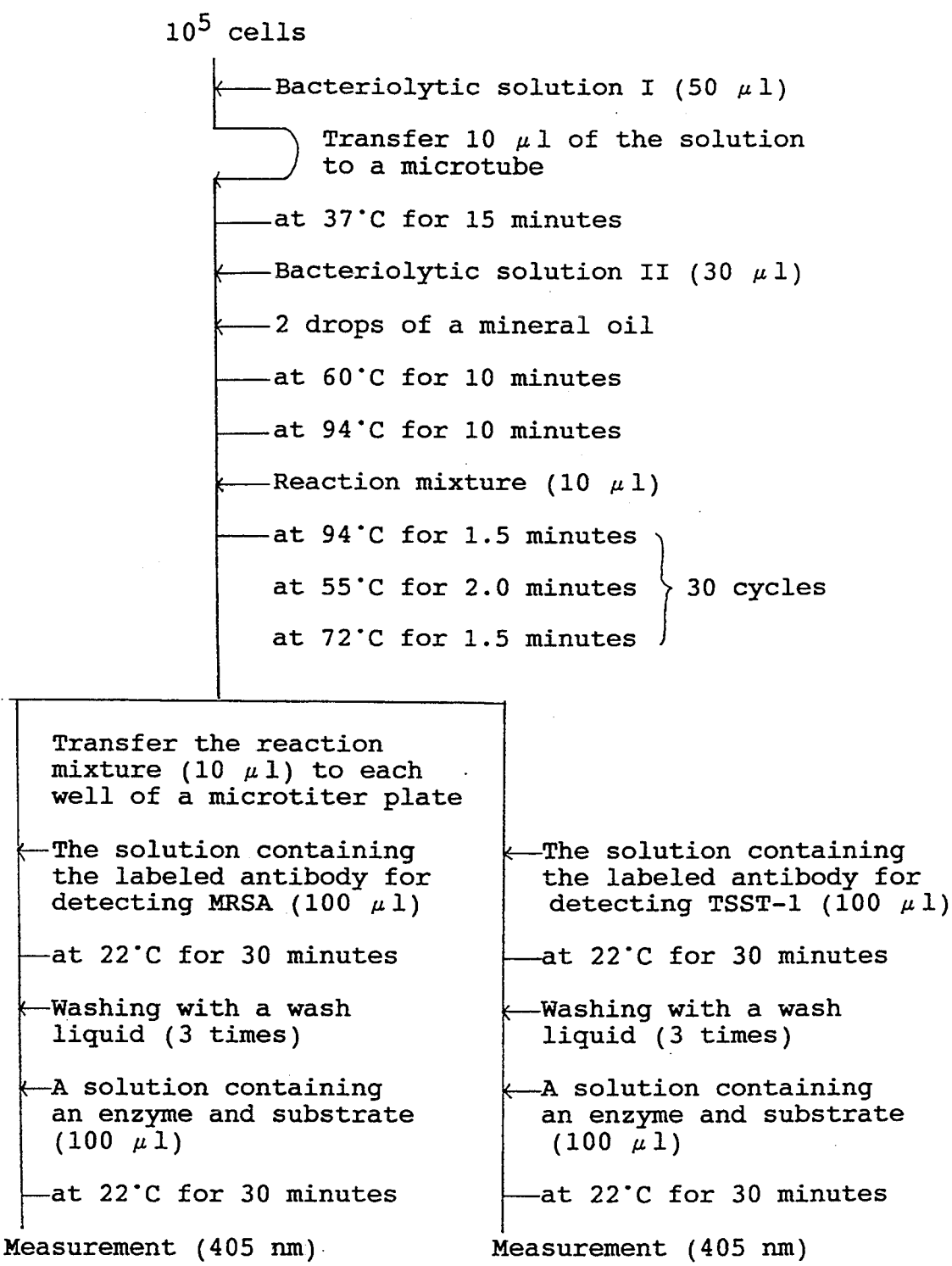

DETECTION FOR STAPHYLOCOCCUS SPP.

BACKGROUND OF THE INVENTION i) Field of the Invention

The present invention relates to a primer for detecting methicillin-resistant and/or toxic shock syndrome toxin 1 producing Staphylococcus spp., a method for detecting these bacteria using the primer, and a kit for detecting them.

ii) Description of the Background Art

Staphylococcus spp. including *Staphylococcus aureus* as a typical bacterium, which have strong pathogenicity, are well known as causative bacteria to various infections. Since these Staphylococcus spp. are generally sensitive to β-lactam series drugs, the infections can be prevented and treated with these drugs. However, a methicillin-resistant Staphylococcus sp. (abbreviated as MRS hereinafter) is so extensively resistant to the β-lactam series drugs that it is difficult to treat infections caused by these methicillin-resistant bacteria. This provides serious problems that the methicillin-resistant bacteria cause opportunistic infections, postoperative infections and the like in the clinical practice.

Since the β-lactam series drugs have high safety and wide antibacterial spectra, some of the β-lactam series drugs are widely used as primary choices of drugs against various infections. The mechanism of these drugs is that binding of the β-lactam series drugs to cell wall-synthesizing enzymes (penicillin-binding proteins: PBPs) which are essential for growth of bacteria results in inhibition of the growth of the bacteria. However, the methicillin-resistant bacteria have changed to produce an additional low-affinity penicillin-binding protein, PBP-2'[Hayes, at al., FEMS Microbial. Lett., 30, 119-122(1981)], which is active at β-lactam concentrations that saturate normal complement of PBPs, so that these bacteria are resistant to β-lactam series drugs.

It is very important to determine whether infectious bacteria are resistant to methicillin in order to set up a therapeutic procedure against the bacteria, and recently susceptibility tests by culturing bacteria have been widely used as methods for detecting MRS. The culturing method, however, requires 2 days to determine the susceptibility. Since some drugs are needed to be administered to patients prior to the determination, incorrect therapy may lead patients to die because effective drugs for MRS are limited. Thus, methods for rapidly detecting MRS should be developed without delay. Moreover, Expression of methicillin resistance in susceptibility tests is subjected to environmental conditions such as temperature [Canawati, H. N. et al. Antimicrob. Agents Chemother. 21, 173-175(1982)], PH [Sabth, L. D. et al. Antimicrob. Agents Chemother, 2, 350-355)] and salt concentration [Chambers, H. F. et al. Antimicrob. Agents Chemother. 31, 1982-1988(1987)]. Conditional expression of PBP-2' may cause ambiguities in susceptibility tests [Barry, A. L. et al. J Clin. Microbiol. 25, 1897-1901(1987)].

Under the present circumstances, researchers have tried to detect MRS by genetic techniques. One of them is an approach that detects the gene for PBP-2' (mecA gene) characterizing MRS [Tomasz et al., Antimicrob. Agents Chemother., 35; 632-639 (1991)]. However, it is difficult to apply the method, which uses the dot hybridization with isotope-labeled DNA probes, in clinical institutes such as hospitals in view of handling. On the other hand, there is another approach [Higashiyama et al., 65th Nippon Kansenshogakkai Kouen Shouroku, p. 13 (1991)] using a polymerase chain reaction [PCR; Mullis et al., Science, 230: 1350-1354 (1985)], which is a highly sensitive and relative rapid method for detecting various genes, though complicated handling and difficult treatment of multiple samples makes the approach unpractical.

Among MRS, strains producing toxic shock syndrome toxin-1 (abbreviated as TSST-1 hereinafter) have been isolated at high frequencies, TSST-1 producing Staphylococcus spp. is abbreviated as TPS hereinafter, and it is said that the mortality of the patients carrying these strains is high. There is a general method for detecting the toxin-producing Staphylococcus spp., which directly detects the toxic protein by the immunological method [See et al., J. Clin. Microbiol. 27:2050-2053 (1989)], and whose sensitivity depends on the amount of toxic proteins produced, being insufficiently used at clinical institutes. The method, which is based on culturing, is also insufficient in view of rapidness. Subsequently, TSST-1 gene was isolated [Schliever et al., J. Biol. Chem., 261: 15783-15786 (1986)]. Although the detection of *Staphylococcus aureus* producing TSST-1 is tried by detecting its gene, this detection method is not practical because of the same reasons as those of the above-mentioned method for detecting MRS.

SUMMARY OF THE INVENTION

Accordingly, it is an object of the present invention to provide a primer for detecting MRS and/or TPS.

It is another object of the present invention to provide a method for detecting MRS and/or TPS.

It is a further object of the present invention to provide a kit for detecting these bacteria.

The above and other objects, features and advantages of the present invention will become apparent from the following description.

BRIEF DESCRIPTION OF THE DRAWINGS

FIG. 2 is a diagram of the procedure for detecting MRSA-producing and TSST-1-producing bacteria at the same time in Example 9.

DETAILED DESCRIPTION OF THE INVENTION AND PREFERRED EMBODIMENTS

Figure 1:
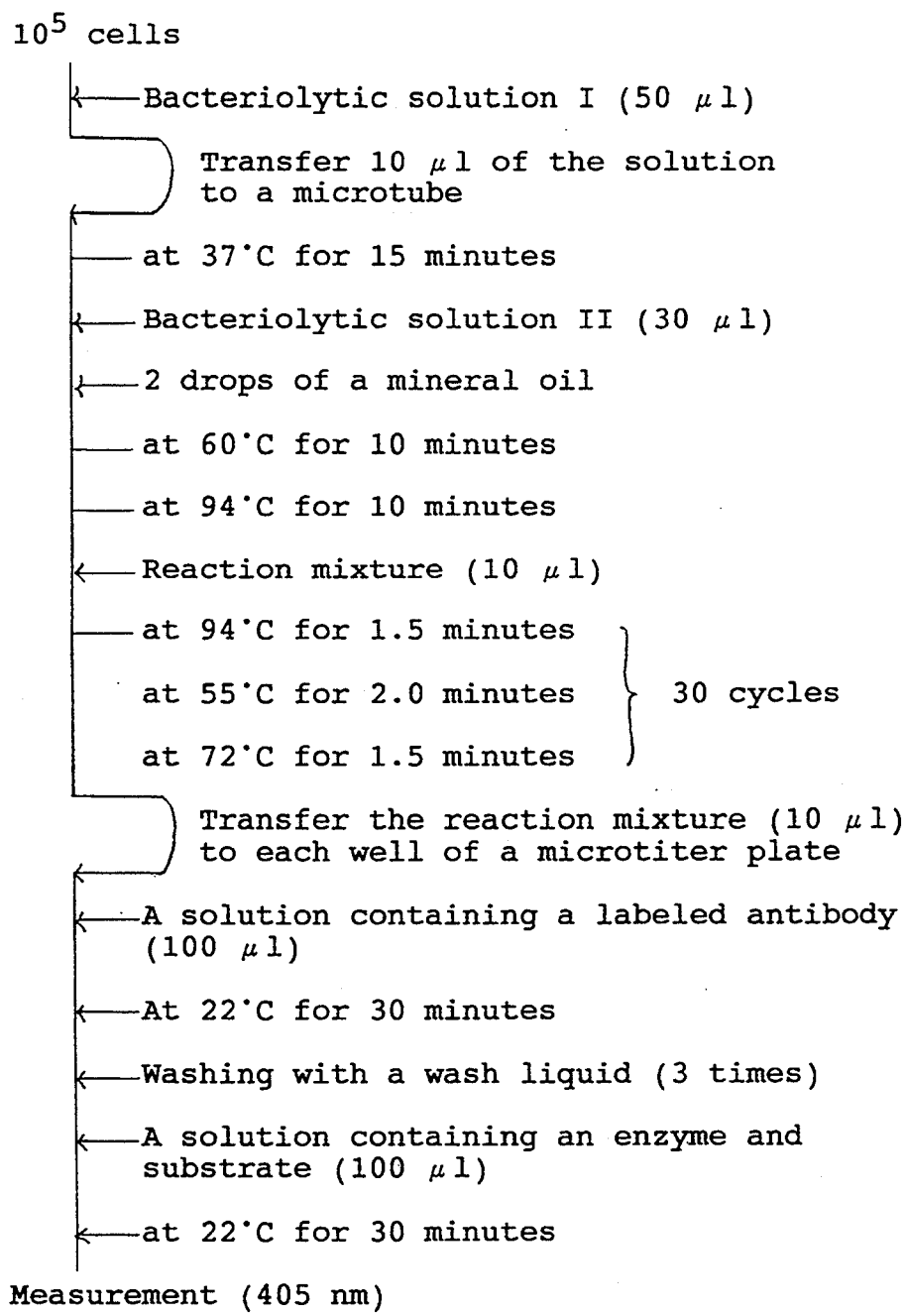
FIG. 1 is a diagram of the procedure for detecting MRSA in Example 7.

The present inventors have studies to overcome the above-mentioned various problems. As a result, the mecA gene, a structural gene for PBP-2', was isolated from a methicillin-resistant *Staphylococcus aureus* [Matsuhashi et al., FEBS Letters 221:167-171 (1987)], and similar genes were isolated from other Staphylococcus spp. which were resistant to ε-lactam series drugs [Antimicrob Agent Chemother., 32:1494-1499 (1988)]. This suggests that the methicillin-resistant staphylococcus spp. can be found by detecting the mecA gene. There are various methods for detecting the gene, and the combinational use of the polymerase chain reaction with them preferably makes highly sensitive detection of the gene successful. In order to achieve these objects, mecA gene seems to be amplified, if primers are designed so as to think much of possibly important regions of the mecA gene sequence. Since PBP-2' coded by the mecA gene, however, has homology to proteins of other pathogenic bacteria and enterobacteria, it is difficult to detect their mecA genes specifically.

The present inventors presumed that the mecA gene comprised a highly homologous region to a part of penicillinase gene and that to a part of the gene for penicillin binding proteins of *Escherichia coli* [Matsuhashi M. et al. FEBS LETTERS, 221, 167–171 (1987)]. As a result of intensive researches to examine various primer sets for gene amplification in view of the boundary region of the mecA gene, the present inventors have found an effective primer set which represent the following base sequences (1) and (2) or their mutation sequences, and which do not react with DNAs of other bacteria (e.g., *Pseudomonas aeruqiuosa*, *Bacillus subtillis* and *Escherichia coli*), yeasts (e.g., *Candida albicans*, *Saccharomyces cerevisiae*) and human, but specifically react with DNA of MRS.

5'GAAATGACTGAACGTCCGAT        (1)

5'GCGATCAATGTTACCGTAGT        (2)

In addition to the above mentioned sequences, a base sequence of the gene coding for the toxic protein of TSST-1 has already been reported [Schlievert et al., J. Biol. Chem., 261:15783–15786 (1986)]. As a result of intensive research to examine different nucleotide fragments which specifically amplify the TSST-1 gene by comparing the base sequence with base sequences of genes of other toxins (SEA, SEB, SEC1, SEC2, SEC3, SED and SEE) which are produced by *Stphylococcus aureus*, the present inventors have found nucleotide fragments which represent the following base sequence (3) and (4) or their mutation sequences.

5'AGTATGGGCCAAAGTTCGAT        (3)

5'CACTTTGATATGTGGATCCG        (4)

Further, the present inventors have found that MRS or TPS can be detected by the polymerase chain reaction using these primers, their labeled sequences or solid support binding-site labeled sequences easily, rapidly and with a high sensitivity.

It is known that more than two genes can be simultaneously amplified (multiple amplification) by the polymerase chain reaction [Chamberlain et al., Nucleic Acids Res. 16:11141-11156 (1988)], though frequencies of nonspecific reactions such as amplification reactions of unexpected gene and amplification reactions of primers one another are very high. The present inventors have found that the use of the primer sets of the present invention does not cause gene products owing to the nonspecific amplification reaction, but can amplify the genes for MRS and TPS simultaneously and specifically, as well as can detect these genes at the same time.

Accomplished on the basis of these findings, the present invention relates to a primer for detecting MRS which comprises the nucleotide fragment of the above-mentioned base sequence (1) or base sequence (2) or its mutation sequence, its labeled sequence or its solid support binding site labeled sequence abbreviated as primer (1) and primer (2), respectively, hereinafter]; a primer for detecting TPS which comprises the nucleotide fragments of the above-mentioned base sequence (3) or base sequence (4) or its mutation sequence, its labeled sequence or its solid support binding site labeled sequence [abbreviated as primer (3) and primer (4), respectively, hereinafter]; and a method and kit for detecting MRS and/or TPS using these primers.

The primers (1) to (4) of the present invention can be prepared by synthesizing chemically, for example, using a DNA synthesizer, or by excising, for example, the gene of MRS or TPS with some enzymes. Examples of MRS used here include *Staphylococcus aureus* (ATCC No. 33591) and the like. Examples of TPS include the bacteria described by Schlievert et al. [J. Biol. Chem. 261:15783–15786 (1986)] and the like.

Any functional primers for detecting the abovementioned Staphylococcus spp. may be used as primers according to the present invention. Examples of these primers include ones in which part of nucleotides are deleted from the nucleotide sequences of the original primers having the above-mentioned nucleotide sequences (1) to (4), ones which are replaced or added by other nucleotides, and more particularly nucleotide sequences which are the corresponding regions of the genes of the mutated strains of the above-mentioned Staphylococcus spp. and the like. It is preferred that there are no mutations, if any, little in the vicinity of the 3'-ends of the primers which seem to greatly affect efficacies of the elongation reaction of the primers, whereas it is allowed that there are mutations in the vicinity of the 5' ends of the primers.

The mutation sequences of primers according to the present invention are not particularly limited so long as the gene amplification is not adversely affected, and it is preferred that the variation of the constituent nucleotides is within 20%.

The labeled sequences of the primers according to the present invention are ones in which the above-mentioned primers are combined with detectable labels. In the present labeling, either non-radioactive or radioactive substances are available as these labels, non-radioactive substances being preferably used. Examples of the non-radioactive substances include fluorescent substances [e.g., fluorescein and its derivatives (fluorescein isothiocyanate and the like), rhodamine and its derivatives (tetramethylrhodamine isothiocyanate, texasred and the like)], chemiluminescent substances (e.g., acridine and the like), delayed fluorescence-emitting substances (DTTA, by Pharmacia) which can be measured directly.

When substances which bind the above-mentioned labels specifically are utilized for detecting these labels, these labels are detected indirectly. Biotin or some haptens are available as these labels. In cases where biotin is used, avidin or streptavidin which specifically binds to biotin can utilized. In cases where haptens are used, antibodies which specifically bind these haptens can be utilized. A compound having a 2,4-dinitrophenol, digoxygenin, biotin and fluorescent substances can be used as haptens. Any of these labels can be introduced into primers singly or, if necessary, in various combination with one another according to the publicly known methods (refer to U.S. Pat. No. 4789737).

Moreover, the solid support binding site of the primers according to the present invention include the primers to which the sites capable of binding to solid support are introduced. For example, the above-mentioned non-radioactive labels also can be used as sites capable of binding to the solid support. The preferred examples include biotin, fluorescent substances such as fluorescein; haptens such as a compound having 2'4-dinitrophenol or digoxygenin. These sites can be introduced into primers according to the present invention in advance singly or, if necessary, in various combination with one another. In order to selectively bind the site to the solid support, the substance for the site should be different from that for the label. The solid support should be inactive against solvents and any reagents to be used, can be separated from the reagents by certain methods, and is able to selectively bind the above-mentioned sites. There are solid support in which streptavidin, antibodies and the like capable of trapping the above-mentioned sites are introduced to solid support such as a microtiter plate, a polystyrene ball, an agarose bead and, a polyacryl bead. The microtiter plate which is excellent in handling and mechanical access is preferably used.

For example, a solid support having streptavidin can be used in order to trap products caused by the polymerase chain reaction with a primer in which biotin is introduced. Moreover, in order to trap products caused by the polymerase chain reaction with a primer in which fluorescein or a 2,4-dinitrophenol is introduced, solid support having the corresponding antibodies can be used.

The method for detecting MRS and/or TPS according to the present invention comprises (a) adding detection primers comprising a combination of primer (1) with primer (2) and/or a combination of primer (3) with primer (4) to a sample containing Staphylococcus spp. so as to cause a polymerase chain reaction: then (b) detecting products caused by the polymerase chain reaction with the detection primers and methicillin-resistant genes and/or toxin-producing genes of Staphylococcus spp. in the sample.

The detection method according to the present invention utilizes the polymerase chain reaction with a set or sets of primers, i.e., a combination of primer (1) with primer (2) and/or a combination of primer (3) with primer (4). Examples of such set of primers include the following (A) to (D):

(A) A set of primers having no modifications;
(B) At least one primer of a set of primers being a labeled sequence;
(C) At least one primer of a set of primers having a solid support binding site; and
(D) One of a set of primers having a solid support binding site and the other being a labeled sequence.

Among them, the combination of (D) is particularly preferred in view of easiness and rapidness in the detection procedure. When the methicillin-resistant gene and toxin-producing gene are detected at the same time using the combination of (D), the label of primer (1) or primer (2) and that of primer (3) or primer (4) should not be the same, provided that the solid support binding site of primer (1) or primer (2) and that of primer (3) or primer (4) is the same. In other words, the label derived from MRS and the label derived from TPS should be distinguished. Therefore, when the methicillin-resistant gene and toxin-producing gene are detected at the same time using the combination of (D), the following embodiments, (i) to (iii), of the primers are preferred.

(i) The solid support-binding site of primer (1) or primer (2) is identical to that of primer (3) or primer (4), and the label of primer (1) or primer (2) is different from that of primer (3) or primer (4).
(ii) The solid support binding site of primer (1) or primer (2) is different from that of primer (3) or primer (4), and the label of primer (1) or primer (2) is identical to that of primer (3) or primer (4).
(iii) The solid support binding site of primer (1) or primer (2) is different from that of primer (3) or primer (4), and the label of primer (1) or primer (2) is different from that of primer (3) or primer (4).

The present invention makes direct and rapid detection of MRS and/or TPS from samples possible, and enabled the patients with infections caused by these bacteria to carry out suitable treatment at an earlier stage.

The detection method according to the present invention will now be described in further detail.

(1) Samples

There are first provided samples to be detected for the presence of the desired MRS and/or TPS. Examples of the samples include cultured medium, bacterial colony, and sputum, urine, pus, blood or various tissue slices obtained from patients.

After a part of a sample is directly collected in case of the colony, or other samples are condensed as precipitates, if necessary, by centrifugation and the like, these samples may be subjected to treatments of lysing cells such as treatments with enzymes, heat surfactants, ultrasonication or combination thereof. The treatment of lysing cells is performed in order to obtain a sufficient amount of DNA derived from Staphylococcus spp. Its practical procedure may be referred to general literatures, for example, "PCR PROTOCOLS" [Academic Press Inc., p. 14 and p. 352 (1989)].

(2) Polymerase chain reaction

If Staphylococcus spp. are present in the abovementioned samples, a polymerase chain reaction according to the elongation reaction of primers may be carried out by adding the primers of the present invention to the samples.

The elongation reaction of a primer can be carried out by introducing four kinds of nucleoside triphosphates (deoxyadenosine triphosphate, deoxyguanosine triphosphate, deoxycytidine triphosphate and thymidine triphosphate: a mixture thereof may be referred to as dNTP) as substrates to the primer.

In the elongation reaction, $E.\ coli$'s DNA polymerase I, Klenow fragments excised by $E.\ coli$'s DNA polymerase I, T4 DNA polymerase and the like are used. If heat-resistant enzymes such as Taq polymerase which cause the elongation reaction at a higher temperature are particularly used, specificity of primers' recognition of a target sequence can be enhanced (referred to U.S. Pat. No. 4889818).

The desired genes of Staphylococcus spp. can be effectively amplified by repeating the elongation reaction using each of two kinds of the primers of the present invention [a combination of primer (1) with primer (2) or a combination of primer (3) with primer (4)].

Further detailed procedure of the polymerase chain reaction should be referred to PCR Technology, Stockton press (1989).

(3) Detection

Detection of a combined substance of the desired gene produced by a primer elongation reaction with a detection primer leads to detection of MRS and/or TPS. The preferred detection method depends on kinds or forms of the above-mentioned primer elongation product, i.e., the synthesized nucleotide chain.

Generally, the product caused by the polymerase chain reaction forms a double stranded DNA, therefore, the synthesized nucleotide chain can be detected by electrophoresis following ethidivm bromide staining [Saiki, R. K. et al., Science, 230:1350–1354 (1985)], dot hybridization with labeled probes [Saiki, R. K. et al., Nature, 324:163–166 (1986)] or the like.

When a label substance is introduced to a synthesized nucleotide chain, the nucleotides can also be detected by the reverse dot hybridization [Saiki, R. K. et al., Proc. Natl. Acad. Sci. USA, 86, 6230–6234 (1989)] in which the labeled and synthesized nucleotide chain is hybridized with the probe immobilized to the solid support, a column method with solid adsorbent (refer to WO89/06285) or the like.

Nucleic acids can be very easily detected by the method described in WO89/06285. That is, there is a method in which products caused by the polymerase chain reaction are contacted with solid supports using the above-mentioned combination of primers (D), and then impurities are washed with an appropriate solvent to remove. Also by this method the desired products with labels which are caused by the polymerase chain reaction are immobilized to the solid support to detect specifically, since the synthesized nucleotide which is elongated by the primer having the solid support binding site forms a double stranded DNA with another synthesized nucleotide which is elongated by the primer having the label.

In fact, the detection of labels may be performed by general methods depending on the labels to be used. For example, in cases where radioisotopes are used as labels, the radioisotopes themselves may be measured. In cases where biotin or a hapten is used as a label, biotin or a hapten can be detected using an avidin (or streptavidin)-enzyme conjugate or an antibody-enzyme conjugate, respectively. The enzyme of the resultant complex (for example, between incorporated biotin and streptavidin-enzyme conjugate) can thus serve as signal reporting moiety. Furthermore, in cases where fluorescent substances are used as labels, emitted fluorescence itself may be measured using a fluorometer.

Moreover, in cases where a label of primer (1) or primer (2) and a label of primer (3) or primer (4) are different from each other for detecting the methicillin-resistant gene and the toxin-producing gene at the same time, the detection procedure of the labels should be performed independently.

The kit for detecting MRS and/or TPS according to the present invention comprises (A) reagents for lysing cells; (B) reagents for causing the polymerase chain reaction which contain the primers consisting of a combination of primer (1) with primer (2) and/or a combination of primer (3) with primer (4); and (C) a solid support for immobilizing products caused by the polymerase chain reaction with the primers for methicillin-resistant genes and/or toxin-producing genes of Staphylococcus spp. Further, the kit of the present invention comprises, if necessary, (D) reagents for indirectly detecting labels, wash liquids and oils. These components will be illustrated below.

(A) Reagents for lysing cells

These reagents contain enzymes for lysing cell walls of Staphylococcus spp., enzymes for hydrolyzing proteins of the bacteria. Any enzymes for lysing cell walls are available which can hydrolyze peptidoglycans of Staphylococcus spp., and so, for example, lysostaphin, acromopeptidase and the like can be used. On the other hand, any enzymes for hydrolyzing proteins are available which can cleave peptide bonds of proteins, and so, for example, trypsin, pepsin or proteinase K and the like can be used. If necessary, surfactants such as Triton X 100, Nonidet P-40, Tween 20 and SDS are optionally added to these enzymes.

(B) Reagents for causing the polymerase chain reaction

These reagents contain the above-mentioned primers for the specified polymerase chain reaction, four different nucleotide triphosphates for synthesizing (amplifying) nucleotide acid chains and an enzyme for nucleic elongation. Optional DNA polymerases can be used as an enzyme for nucleotide acid elongation, and so the use of a heat-stable DNA polymerase can preferably cause a rapid and specific polymerase chain reaction. Examples of these polymerases include Taq DNA polymerase, Tth DNA polymerase and Vent DNA polymerase and the like.

(C) Solid support for immobilizing products caused by a polymerase chain reaction As described above in detail, these solid supports can specifically bind to the solid support binding sites which are introduced to the primers of the present invention. Microtiter well which is treated so as to bind specifically to the site, is preferably used.

(D) Other reagents

Any wash liquids are not particularly limited if these remove unreacted primers, reagents and the like, as well as do not affect the detection reaction. In general, buffers can be used.

Among oils, an oil can be used which prevents evaporation of water in the reaction solution and can separate water, and has smaller specific gravity than water. Examples of the oils include silicone oil, mineral oil and the like.

In cases where labels not capable of directly detecting are introduced to primers, reagents for detecting labels are those containing reagents indirectly detecting these labels. For example, in cases where a label is a hapten, these reagents are (a) those of enzyme conjugated-antibodies specific to the hapten, (b) the substrates of the enzymes and the like. Examples of these reagents include: 2-nitrophenyl-$\beta$-D-galactopyranoside, 4-methylumbelliferyl-$\epsilon$-D-galactopyranoside and the like as substrates in case where the enzyme is $\epsilon$-D-galactosidase; 3-(4-hydroxyphenyl) propionic acid, 3,3',5,5'-tetramethylbenzidine, 1,2-phenylenediamine and the like as substrates in case where the enzyme is peroxydase; 4-methylumbelliferyl phosphate, NADP, 4-nitrophenyl phosphate and the like as substrates in case where the enzyme is alkaline phosphatase; glucose, NAD and the like as substrates in case where the enzyme is glucose-6-phosphate dehydrogenase; ethanol, NAD and the like as substrates in case where the enzyme is alcohol dehydrogenase.

EXAMPLES

The present invention is illustrated with reference to the following examples, but the invention is not intended to be limited only to the Examples.

Example 1

Preparation of primers

In accordance with the present invention, the primers to which labels or solid support binding sites were introduced, or primers to which labels or solid support binding sites were not introduced were chemically synthesized by the following method.

First, in cases where the primers to which labels or solid support binding sites were not introduced, these primers were chemically synthesized by the phosphoamidite method of Caruthers et al. [Tetrahedron Lett. 22:1859 (1981)] using an Applied Biosystems Model 381A DNA synthesizer in an amount scale of 0.2 $\mu$mole.

On the other hand, in cases where the primers to which labels or solid support binding sites were introduced, oligonucleotides whose 5'-ends had amino groups introduced were synthesized, and then labels or solid support binding sites were introduced to them with appropriate reagents. The following examples explain these syntheses in detail.

First, an oligonucleotide (5'GAAATGACTGAACGTCCGAT) whose 5'lends had an amino group introduced was synthesized using an Applied Biosystems Model 381A DNA synthesizer. Protective mononucleotide phosphoamidites were subsequently added to 0.2 μmole of a solid support and Aminolink II (tradename, Applied Byosystems) was added in the final step. Then these substances were liberated from the solid support by treatment with concentrated ammonia and protective groups were removed.

After deprotection, the liberated mixture was applied to gel filtration with Sephadex G-50, and then fractions of the peak eluted first were collected to condense. The sample was then purified by reverse-phase HPLC (column: μ-Bondapak C18; eluent: 5–20% acetonitrile/50 mM triethylammonium acetic acid, pH 7.0).

Then a 1M $NaHCO_3$ solution (10 μl), $H_2O$ (30 μl) and a solution of biotin-N-hydroxysuccinimide ester (BRL Co., Ltd) in DMF (20 μg/μl, 50 μl) were added to a solution of aminated oligonucleotide (1 O.D.: 10 μl, which were mixed and allowed to stand at room temperature. After 4 hours, the mixture was applied to gel filtration column (Sephadex G-50), was eluted with 50 mM TEAB buffer (a solution of triethylammonium bicarbonate, pH 7.5), and then fractions of the peak eluted first were collected to dry into solid (yield: 0.6 O.D.).

If aminated oligonucleotide as a starting material was crude, or biotinylation reaction did not proceed quantitatively, samples obtained after gel filtration were purified further by reverse-phase HPLC (column: μ-Bondapak C18; eluent: 5–20% acetonitrile/50 mM triethylammonium acetic acid, pH 7.0). In this case, since the desired biotinylated oligonucleotide elutes later than starting material and the other impurities, it can be easily purified.

An oligonucleotide (5'GCGATCAATGTTACCGTAGT) whose 5'-ends had a dinitrophenyl group (DNP) introduced was derived from that whose 5'-ends had an amino group introduced, and used as a starting material as in case of the biotinylated oligonucleotide.

A 1M $NaHCO_3$ solution (20 μl) was added to a solution of an aminated oligonucleotide solution (2 O.D.: 180 μl), to which an ethanol solution of dinitrofluorobenzene (5% (v/v), 100 ul) was added, and then the solution was heated for 2 hours at 37° C. After completion of the reaction, the solution was applied to gel filtration to remove reagents and purified (yield: 1.2 O.D.).

An oligonucleotide (5'CACTTTGATATGTGGATCCG) whose 5'-ends had a fluorescein group introduced was derived from that whose 5'-ends had an amino group introduced, and used as a starting material as in case of the biotinated oligonucleotide.

A 1M $Na_2CO_3$ solution (108 μl) and water (120 μl) was added to a solution of an aminated oligonucleotide solution (2 O.D.: 40 μl), to which an solution of fluorescein isothiocyanate (4 mg/12 ul) in DMF was added, and then the solution was mixed to react at room temperature over night. After completion of the reaction, the solution was applied to gel filtration to remove reagents and purified by HPLC (yield: 0.85 O.D.).

Example 2

Labeling of antibody

Anti-DNP antibody and Anti-FITC antibody were prepared by standard method. In brief, each hapten was conjugated with keyhole limpet's hemocyanin (KLH), and then rabbits were immunized with these conjugates. These antisera obtained from these rabbits were purified by salting out with ammonium sulfate and by affinity chromatography. The purified antibodies were digested to Fab's, which were labeled with N-(ε-maleimide caproic acid) succinimide (EMCS) as a crosslinking agent by alkaline phosphatase.

Example 3

Preparation of streptavidin-immobilized wells of a microtiter plate

Phosphate buffered saline (PBS) supplemented with glutaraldehyde up to 2% was added to aminated wells of a microtiter plate (Sepaplate 8F Amino type, Sumitomo Bakelite Co., Ltd.) (100 μl/well), which was reacted at 37° C. for 4 hours. After completion of the reaction, the wells were washed with water 2 times, to which streptavidin solution in carbonate buffer (10 ug/ml, 10 mM $NaHCO_3$-$Na_2CO_3$, pH 9.5) was added (100 ul/well), and then the plate was reacted at 37° C. for 4 hours.

After completion of the reaction, the wells were washed with PBS, to which 1% BSA, 0.05% $NaN_3$ and PBS⁻, and then the plate was kept at 4° C.

Example 4 mecA gene-specific amplification reaction

When DNAs from *P. aeruqinosa, B. subtilis, E. coli, S. aureus*, methicillin-resistant *S. aureus* and human, which were prepared according to a conventional manner were provided as samples, and their genes were amplified by the PCR method. The DNA sample (100 ng, but 1 ug for human DNA) was added to 100 ul of a reaction mixture containing 2 kinds of primers (biotin-GAAATGACTGAACGTCCGAT and DNP-GCGATCAATGTTACCGTAGT, 100 ng each), dATP, dGTP, dCTP and TTP (200 μM each), 100 mM Tris-HCl (pH 8.3), 50 mM KCl, 1.5 mM $MgCl_2$, and 0.01% gelatin. Heated at 94° C. for 5 min., the mixture was kept at 50° C. for 5 min. Then 2.5 units of heat-resistant DNA polymerase (Cettus Co., Ltd.) were added to the mixture, which was reacted at 72° C. for 60 sec., at 94° C. for 30 sec. and at 50° C. for 30 sec. as 1 cycle for 30 cycles.

After completion of the reaction, 5 μl of the resulting mixture was subjected to agarose gel electrophoresis, and then amplified nucleotide chains were detected by ethidium bromide-staining. As a result, when the DNA of methicillin-resistant *Staphylococcus aureus* was used as a sample, a band corresponding to the expected amplified nucleotide chain of 150 base pairs was able to be identified. On the other hand, when DNAs obtained from *P. aeruginosa, B. subtilis, E. Coli, S. aureus* and human were used as samples, bands corresponding to the expected amplified nucleotide chains were not able to be identified.

Example 5

TSST-1 gene-specific amplification reaction

The cross-reactivities of the TSST-1 gene-specific primers (biotin-AGTATGGGCCAAAGTTCGAT and DNP-CACTTTGATATGTGGATCCG) with other bacterial strains were tested as in Example 4. DNAs obtained from *P. aeruqinosa, B. subtilis, E. coli,* TSST-1-producing *S. aureus* and human were used as samples. When the TSST-1-producing *S. aureus* was used, a band corresponding to the expected amplified nucleotide chain of 159 base pairs was able to be identified. When the other DNAs were used, bands corresponding to the expected amplified nucleotide chains were not able to be identified.

Example 6 mecA gene- and TSST-1 gene-specific amplification reaction at the same time

The mecA gene-specific primers (biotin-GAAAT-GACTGAACGTCCGAT) and DNP-GCGAT-CAATGTTACCGTAGT) and TSST-1-gene-specific primers (biotin-AGTATGGGCCAAAGTTCGAT and DNP-CACTTTGATATGTGGATCCG) were used at each amount of 100 ng, and these primers were subjected to the polymerase chain reaction as under the conditions in Example 4. DNA samples were prepared from *P. aeruqinosa, B. subtilis, E. coli, S. aureus,* methicillin-resistant *S. aureus*, TSST-1-producing *S. aureus* and human. As a result of the reaction, when the DNA of methicillin-resistant *Staphylococcus aureus* was used as a sample, only a band corresonding to 150 base pairs was able to be identified and when the DNA of TSST-1 producing *S. aureus* was used as a sample, only a band corresponding to 159 base pairs was able to be identified. On the other hand, when the DNA of methicillin-resistant and TSST-1-producing *Staphylococcus aureus* were used, only two bands corresponding to 150 base pairs and 159 base pairs were able to be identified. No bands were identified when DNAs except the above-mentioned ones were used.

Example 7

Detection of MRSA in clinically isolated strains using the kit for detecting MRS The four strains whose characters had been elucidated by the culturing method were tested for methicillin-resistance using the kit of the present invention. Each clinically isolated strain was prepared so as to reach a density of $10^5$ cells per reaction, and subjected to the detection procedure according to the method shown in FIG. 1. The results are shown in Table 1.

TABLE 1

|  | MRSA | TSST-1 | Measurements |
|---|---|---|---|
| Clinically isolated strain 1 | − | + | 0.02 |
| Clinically isolated strain 2 | − | − | 0.02 |
| Clinically isolated strain 3 | + | + | 0.34 |
| Clinically isolated strain 4 | + | − | 0.70 |

Example 8

Detection of TSST-1-producing *Staphylococcus aureus* in clinically isolated strains using the kit for detecting TSST-1-producing *Staphylococcus aureus*

The same four strains which had been clinically isolated as in Example 7 were tested for TSST-1-production using the kit of the present invention. $10^5$ cells of each strain were subjected to the detection procedure according to the method shown in FIG. 1 as in Example 7. The results are shown in Table 2.

TABLE 2

|  | MRSA | TSST-1 | Measurements |
|---|---|---|---|
| Clinically isolated strain 1 | − | + | 0.23 |
| Clinically isolated strain 2 | − | − | 0.01 |
| Clinically isolated strain 3 | + | + | 0.30 |
| Clinically isolated strain 4 | + | − | 0.02 |

Example 9

Analysis of clinically isolated strains using the kit for detecting methicillin-resistant and TSST-1-producing *Staphylococcus aureus* at the same time The same four strains which had been clinically isolated as in Example 7 were tested for methicillin-resistance or TSST-1-production using the kit of the present invention. $10^5$ cells of each strain were subjected to the detection procedure according to the method shown in FIG. 1. The results are shown in Table 3.

TABLE 3

|  |  |  | Measurements | |
|---|---|---|---|---|
|  | MRSA | TSST-1 | MRSA | TSST-1 |
| Clinically isolated strain 1 | − | + | 0.00 | 0.36 |
| Clinically isolated strain 2 | − | − | 0.00 | 0.00 |
| Clinically isolated strain 3 | + | + | 0.30 | 0.33 |
| Clinically isolated strain 4 | + | − | 0.74 | 0.00 |

What is claimed is:

1. A kit for detecting in a sample Staphylococcus spp. carrying the mec A gene and encoding the tsst-1 gene which comprises (a) a reagent for causing a polymerase chain reaction which contains a detection primer composition consisting essentially of
  (i) a nucleotide fragment of sequence (1)

5'GAAATGACTGAACGTCCGAT           (1), a labeled sequence thereof, or a solid support binding-site labeled sequence thereof;
   (ii) a nucleotide fragment of sequence (2):

5'GCGATCAATGTTACCGTAGT       (2), a labeled sequence thereof, or a solid support binding-site labeled sequence thereof;
   (iii) a nucleotide fragment of sequence (3):

5'AGTATGGGCCAAAGTTCGAT       (3), a labeled sequence thereof, or a solid support binding-site labeled sequence thereof; and
   (iv) a nucleotide fragment of sequence (4):

5'CACTTTGATATGTGGATCCG       (4), a labeled sequence thereof, or a solid support binding-site labeled sequence thereof; and
   (b) a solid support for immobilizing products caused by a polymerase chain reaction with the primer composition.
2. The kit according to claim 1 further comprising a reagent for lysing the cells in the sample.
3. The kit according to claim 1 further comprising nucleoside triphosphates selected from the group consisting of deoxyadenosine triphosphate, deoxyguanosine triphosphate, deoxycytidine triphosphate, thymidine triphosphate, and mixtures thereof.
4. The kit according to claim 1 wherein the Staphylococcus spp. is *Staphylococcus aureus*.
5. The kit according to claim 1 wherein the labeled sequence is labeled with biotin or a hapten.
6. A method for the simultaneous and specific detection of Staphylococcus spp. carrying the mec A gene and encoding the tsst-1 gene in a cell-containing sample, which method comprises a polymerase chain reaction resulting from
   (a) adding to the sample a primer composition consisting essentially of:
   (i) a nucleotide fragment of sequence (1):

5'GAAATGACTGAACGTCCGAT       (1), a labeled sequence thereof, or a solid support binding-site labeled sequence thereof;
   (ii) a nucleotide fragment of sequence (2):

5'GCGATCAATGTTACCGTAGT       (2), a labeled sequence thereof, or a solid support binding-site labeled sequence thereof;
   (iii) a nucleotide fragment of sequence (3):

5'AGTATGGGCCAAAGTTCGAT       (3), a labeled sequence thereof, or a solid support binding-site labeled sequence thereof; and
   (iv) a nucleotide fragment of sequence (4):

5'CACTTTGATATGTGGATCCG       (4), a labeled sequence thereof, or a solid support binding-site labeled sequence thereof;
   (b) adding nucleoside triphosphates to the sample to cause an elongation reaction of the primer composition; and
   (c) repeating the elongation reaction of step (b) to amplify the genes; followed by detection of the genes.
7. A method according to claim 6 wherein the Staphylococcus spp. is Staphylococcus aureus.
8. A method according to claim 7 wherein cells in the sample are lysed in advance.
9. A method according to claim 7 wherein the nucleoside triphosphates are selected from the group consisting of deoxyadenosine triphosphate, deoxyguanosine triphosphate, deoxycytidine triphosphate, thymidine triphosphate, and mixtures thereof.
10. A method according to claim 7 wherein nucleotide fragments of sequences (1) and (2) are combined and have a solid support binding site, and the nucleotide fragments of sequences (3) and (4) are combined and are labeled.
11. A method according to claim 7 wherein nucleotide fragment of sequences (1) and (2) are combined and are labeled, and the nucleotide fragments of sequences (3) and (4) are combined and have a solid support binding site.
12. A method for detecting methicillin-resistant and toxic shock syndrome toxin-1 producing Staphylococcus spp. in a cell-containing sample by a polymerase chain reaction wherein the method comprises
   (a) adding to the sample a detection primer composition consisting essentially of
   (i) a nucleotide fragment of sequence (1):

5'GAAATGACTGAACGTCCGAT       (1), a labeled sequence thereof, or a solid support binding-site labeled sequence thereof;
   (ii) a nucleotide fragment of sequence (2):

5'GCGATCAATGTTACCGTAGT       (2), a labeled sequence thereof, or a solid support binding-site labeled sequence thereof;
   (iii) a nucleotide fragment of sequence (3):

5'AGTATGGGCCAAAGTTCGAT       (3), a labeled sequence thereof, or a solid support binding-site labeled sequence thereof; and
   (iv) a nucleotide fragment of sequence (4):

5'CACTTTGATATGTGGATCCG       (4), a labeled sequence thereof, or a solid support binding-site labeled sequence thereof; then
   (b) detecting products caused by the polymerase chain reaction with the detection primer composition and methicillin-resistant genes and toxin-producing genes of Staphylococcus spp. in the sample.
13. The method according to claim 12 wherein the methicillin-resistant and toxic shock syndrome toxin-1 producing Staphylococcus spp. is *Staphylococcus aureus*.
14. The method according to claim 12 wherein cells in the sample are lysed in advance.
15. A primer composition for the simultaneous and specific detection of Staphylococcus spp. in a sample carrying the mec A gene and encoding the tsst-1 gene in a cell-containing sample, consisting essentially of
   (i) a nucleotide fragment of sequence (1):

5'GAAATGACTGAACGTCCGAT       (1)

a labeled sequence thereof, or a solid support binding-site labeled sequence thereof;

(ii) a nucleotide fragment of sequence (2):

5'GCGATCAATGTTACCGTAGT  (2), a labeled sequence thereof, or a solid support binding-site labeled sequence thereof;

(iii) a nucleotide fragment of sequence (3):

5'AGTATGGGCCAAAGTTCGAT  (3), a labeled sequence thereof or a solid support binding-site labeled sequence thereof; and (iv) a nucleotide fragment of sequence (4):

5'CACTTTGATATGTGGATCCG  (4), a labeled sequence thereof or a solid support binding-site labeled sequence thereof.

16. The primer composition according to claim 15 wherein the labeled sequence is labeled with biotin or a hapten.

17. A primer for specifically detecting methicillin-resistant Staphylococcus spp. consisting of a nucleotide fragment of sequence (1):

5'GAAATGACTGAACGTCCGAT  (1), a labeled sequence thereof, or a solid support binding-site labeled sequence thereof, which sequence specifically reacts with DNA of the methicillin-resistant strain of Staphylococcus spp.

18. A primer for specifically detecting methicillin-resistant Staphylococcus spp. consisting of a nucleotide fragment of sequence (2):

5'GCGATCAATGTTACCGTAGT  (2), a labeled sequence thereof, or a solid support binding-site labeled sequence thereof, which sequence specifically reacts with DNA of the methicillin-resistant strain of Staphylococcus spp.

19. A primer for specifically detecting toxic shock syndrome toxin-1 producing strains of Staphylococcus spp. consisting of a nucleotide fragment of sequence (3):

5'AGTATGGGCCAAAGTTCGAT  (3), a labeled sequence thereof, or a solid support binding-site labeled sequence thereof, which sequence specifically amplifies DNA of toxic shock syndrome producing toxin-1 strains of Staphylococcus spp.

20. A primer for specifically detecting toxic shock syndrome toxin-1 producing strains of Staphylococcus spp. consisting of a nucleotide fragment of sequence (4):

5'CACTTTGATATGTGGATCCG  (4), a labeled sequence thereof, or a solid support binding-site labeled sequence thereof, which sequence specifically amplifies DNA of toxic shock syndrome producing toxin-1 strains of Staphylococcus spp.

* * * * *

SEQUENCE LISTING ( 1 ) GENERAL INFORMATION:

( i i i ) NUMBER OF SEQUENCES: 4

( 2 ) INFORMATION FOR SEQ ID NO: 1 :

( i ) SEQUENCE CHARACTERISTICS:
      ( A ) LENGTH: 20
      ( B ) TYPE: Nucleic acid
      ( C ) STRANDEDNESS: Single
      ( D ) TOPOLOGY: Linear ( i i ) MOLECULE TYPE: Other nucleic acid (Synthetic nucleic acid)

( i i i ) HYPOTHETICAL: No ( i v ) ANTI-SENSE: No ( v i ) ORIGINAL SOURCE:

(A) ORGANISM: methicillin resistant *Staphylococcus aureus*

(xi) SEQUENCE DESCRIPTION: SEQ ID NO: 1:

GAAATGACTG AACGTCCGAT           20

(2) INFORMATION FOR SEQ ID NO: 2:

(i) SEQUENCE CHARACTERISTICS:
  (A) LENGTH: 20
  (B) TYPE: Nucleic acid
  (C) STRANDEDNESS: Single
  (D) TOPOLOGY: Linear (ii) MOLECULE TYPE: Other nucleic acid (Synthetic nucleic acid)

(iii) HYPOTHETICAL: No (iv) ANTI-SENSE: Yes (vi) ORIGINAL SOURCE:
  (A) ORGANISM: methicillin resistant *Staphylococcus aureus*

(xi) SEQUENCE DESCRIPTION: SEQ ID NO: 2:

GCGATCAATG TTACCGTAGT           20

(2) INFORMATION FOR SEQ ID NO: 3:

(i) SEQUENCE CHARACTERISTICS:
  (A) LENGTH: 20
  (B) TYPE: Nucleic acid
  (C) STRANDEDNESS: Single
  (D) TOPOLOGY: Linear (ii) MOLECULE TYPE: Other nucleic acid (Synthetic nucleic acid)

(iii) HYPOTHETICAL: No (iv) ANTI-SENSE: No (vi) ORIGINAL SOURCE:
  (A) ORGANISM: toxic shock syndrome toxin 1 producing
    *Staphylococcus aureus*

(xi) SEQUENCE DESCRIPTION: SEQ ID NO: 3:

AGTATGGGCC AAAGTTCGAT           20

(2) INFORMATION FOR SEQ ID NO: 4:

(i) SEQUENCE CHARACTERISTICS:
  (A) LENGTH: 20
  (B) TYPE: Nucleic acid
  (C) STRANDEDNESS: Single
  (D) TOPOLOGY: Linear (ii) MOLECULE TYPE: Other nucleic acid (Synthetic nucleic acid)

(iii) HYPOTHETICAL: No (iv) ANTI-SENSE: Yes (vi) ORIGINAL SOURCE:
  (A) ORGANISM: toxic shock syndrome toxin 1 producing
    *Staphylococcus aureus*

(xi) SEQUENCE DESCRIPTION: SEQ ID NO: 4:

CACTTTGATA TGTGGATCCG           20